United States Patent
Sweeney et al.

(10) Patent No.: US 7,392,090 B2
(45) Date of Patent: *Jun. 24, 2008

(54) DATA LOGGING SYSTEM FOR IMPLANTABLE MEDICAL DEVICE

(75) Inventors: Robert J. Sweeney, Woodbury, MN (US); Avram Scheiner, Vadnais Heights, MN (US); Ronald W. Heil, Jr., Roseville, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 860 days.

This patent is subject to a terminal disclaimer.

(21) Appl. No.: 10/672,315

(22) Filed: Sep. 26, 2003

(65) Prior Publication Data

US 2004/0059391 A1  Mar. 25, 2004

Related U.S. Application Data

(63) Continuation of application No. 09/740,258, filed on Dec. 18, 2000, now Pat. No. 6,628,985, and a continuation-in-part of application No. 09/999,260, filed on Nov. 30, 2001, now Pat. No. 7,201,733, which is a continuation of application No. 09/422,433, filed on Oct. 21, 1999, now Pat. No. 6,361,522.

(51) Int. Cl.
*A61N 1/00* (2006.01)

(52) U.S. Cl. ............... 607/60; 600/510; 600/515; 607/30

(58) Field of Classification Search ............ 607/32, 607/60, 61; 128/903
See application file for complete search history.

(56) References Cited

U.S. PATENT DOCUMENTS

| 4,137,908 | A | * | 2/1979 | Degonde et al. | 600/510 |
|---|---|---|---|---|---|
| 4,281,664 | A | | 8/1981 | Duggan | 128/696 |
| 4,556,063 | A | * | 12/1985 | Thompson et al. | 607/32 |
| 4,944,299 | A | | 7/1990 | Silvian | 128/419 PG |
| 4,987,897 | A | | 1/1991 | Funke | 128/419 PG |
| 5,058,581 | A | | 10/1991 | Silvian | 128/419 PG |
| 5,127,404 | A | | 7/1992 | Wyborny et al. | 128/419 P |
| 5,190,035 | A | | 3/1993 | Salo et al. | 128/419 |
| 5,342,408 | A | | 8/1994 | deCoriolis et al. | 607/32 |
| 5,416,695 | A | | 5/1995 | Stutman et al. | 364/413.02 |
| 5,456,692 | A | | 10/1995 | Smith, Jr. et al. | 607/31 |
| 5,562,713 | A | | 10/1996 | Silvian | 607/32 |
| 5,579,876 | A | | 12/1996 | Adrian et al. | 188/322.17 |
| 5,586,556 | A | | 12/1996 | Spivey et al. | 128/697 |
| 5,720,770 | A | | 2/1998 | Nappholz et al. | 607/30 |
| 5,759,199 | A | * | 6/1998 | Snell et al. | 607/60 |
| 5,792,204 | A | * | 8/1998 | Snell | 607/32 |
| 5,906,633 | A | | 5/1999 | Mouchawar et al. | 607/5 |
| 6,115,636 | A | | 9/2000 | Ryan | 607/60 |

(Continued)

*Primary Examiner*—Carl H. Layno
*Assistant Examiner*—Brian T Gedeon
(74) *Attorney, Agent, or Firm*—Schwegman, Lundberg & Woessner, P.A.

(57) ABSTRACT

A data logging system and method in which an implantable medical device transmits logged data to an external data logging device with low energy potential signals. The implantable device generates potential signals modulated with digitally encoded data by operating a current source to cause corresponding electrical potentials that can be sensed at the skin surface by the external data logging device. The data logging device then demodulates the sensed potentials to derive the digital data and stores the data in a data logging storage medium.

18 Claims, 5 Drawing Sheets

U.S. PATENT DOCUMENTS

| | | | |
|---|---|---|---|
| 6,212,434 B1 | 4/2001 | Scheiner et al. | 607/123 |
| 6,256,541 B1 | 7/2001 | Heil et al. | 607/123 |
| 6,272,377 B1 | 8/2001 | Sweeney et al. | 600/515 |
| 6,285,909 B1 | 9/2001 | Sweeney et al. | 607/32 |
| 6,298,269 B1 | 10/2001 | Sweeney | 607/28 |
| 6,321,122 B1 | 11/2001 | Scheiner et al. | 607/122 |
| 6,361,522 B1 | 3/2002 | Scheiner et al. | 604/67 |
| 6,363,281 B1 | 3/2002 | Zhu et al. | 607/28 |
| 6,400,982 B2 | 6/2002 | Sweeney et al. | 600/515 |
| 6,415,183 B1 | 7/2002 | Scheiner et al. | 607/42 |
| 6,628,985 B2 * | 9/2003 | Sweeney et al. | 600/510 |
| 7,302,294 B2 * | 11/2007 | Kamath et al. | 607/6 |

\* cited by examiner

DATA LOGGING SYSTEM FOR IMPLANTABLE MEDICAL DEVICE

This application is a continuation of U.S. patent application Ser. No. 09/740,258, filed on Dec. 18, 2000, now issued as U.S. Pat. No. 6,628,985, and a continuation-in-part of U.S. patent application Ser. No. 09/999,260, filed on Nov. 30, 2001, now issued as U.S. Pat. No. 7,201,733 which is a continuation of U.S. patent application Ser. No. 09/422,433, filed on Oct. 21, 1999, now issued as U.S. Pat. No. 6,361,522, the disclosures of which are hereby incorporated by reference.

FIELD OF THE INVENTION

This invention pertains to implantable medical devices such as cardiac pacemakers and implantable cardioverter/defibrillators. In particular, the invention relates to a system and method enabling an implantable medical device to communicate information to an external data logging device.

BACKGROUND

Implantable medical devices are commonplace today, particularly for treating cardiac dysfunction. Cardiac pacemakers, for example, are implantable medical devices that replace or supplement a heart's compromised ability to pace itself (i.e., bradycardia) due to chronotropic incompetence or a conduction system defect by delivering electrical pacing pulses to the heart. Implantable cardioverter/defibrillators (ICD's) are devices that deliver electrical energy to the heart in order to reverse excessively rapid heart rates (tachycardia) including life threatening cardiac arrhythmias such as ventricular fibrillation. Since some patients have conditions that necessitate pacing and also render them vulnerable to life-threatening arrhythmias, implantable cardiac devices have been developed that combine both functions in a single device.

Most pacemakers today are operated in some sort of synchronous mode where the pacing pulses are delivered in a manner that is dependent upon the intrinsic depolarizations of the heart as sensed by the pacemaker. ICD's must also sense the electrical activity of the heart in order to detect an arrhythmia that will trigger delivery of the shock pulse in an attempt to reverse the condition. Such sensed information can be stored by the device in the form of a data log which can be transferred later to an external programmer via a radio link. Due to the limited data storage capacity in a typical implanted device, however, only a small fraction of the total sensed information is actually stored in the data log. One way to circumvent this problem would be to transmit the data log continuously or at frequent intervals to the external programmer. An implantable device has only a battery power supply, however, and the energy costs of such frequent radio transmissions would be excessive. What is needed is a low-energy data transmission method so that the implantable device can transmit logged data either continuously or at frequent intervals to an external device. It is toward this objective that the present invention is primarily directed.

SUMMARY OF THE INVENTION

The present invention relates to a data logging system and method in which an implantable medical device transmits data to an external data logging device with low energy potential signals. The implantable device generates potential signals by operating a current source to cause corresponding electrical potentials that can be sensed at the skin surface by the external data logging device. The current source is operated so as to generate a carrier waveform that can be modulated with digitally encoded information corresponding to sensed data logged by the implantable device. The external data logging device includes electrodes at the skin surface for sensing potentials and circuitry for demodulating the sensed carrier waveform to derive the encoded logged data. The data logging device may then store the digital data in a storage medium for later retrieval. The storage medium is preferably a non-volatile memory that can be removed and replaced at periodic intervals. Alternatively, the contents of the storage medium can be directly transferred to another device at periodic intervals.

In accordance with the invention, the carrier waveform is digitally modulated with the digitally encoded information by varying the amplitude or frequency of the carrier waveform using, for example, amplitude shift-keying or frequency shift-keying. In a particular embodiment, a digital pulse train is modulated with the digitally encoded information by varying the frequency, width, or position of the pulses. The pulse train is then used to amplitude modulate the carrier waveform.

Certain implantable medical devices, such as rate-adaptive pacemakers, may use an impedance technique for measuring minute ventilation and/or cardiac stroke volume. In that technique, an oscillating current is made to flow between two electrodes located within the thorax, and the impedance between the electrodes is measured. In accordance with the invention, the impedance measuring current may be used as the carrier waveform and modulated with digitally encoded information by the implantable device for transmission to the external data logging device.

The present invention may be incorporated into a system where the implantable device is a cardiac device such as an implantable cardioverter/defibrillator, cardiac pacemaker, or combination device. In one embodiment, the data logging device is a self-contained unit in the form of a patch designed for external affixation to a patient's skin surface at a suitable location.

DESCRIPTION OF A SPECIFIC EMBODIMENT

Figure 1:
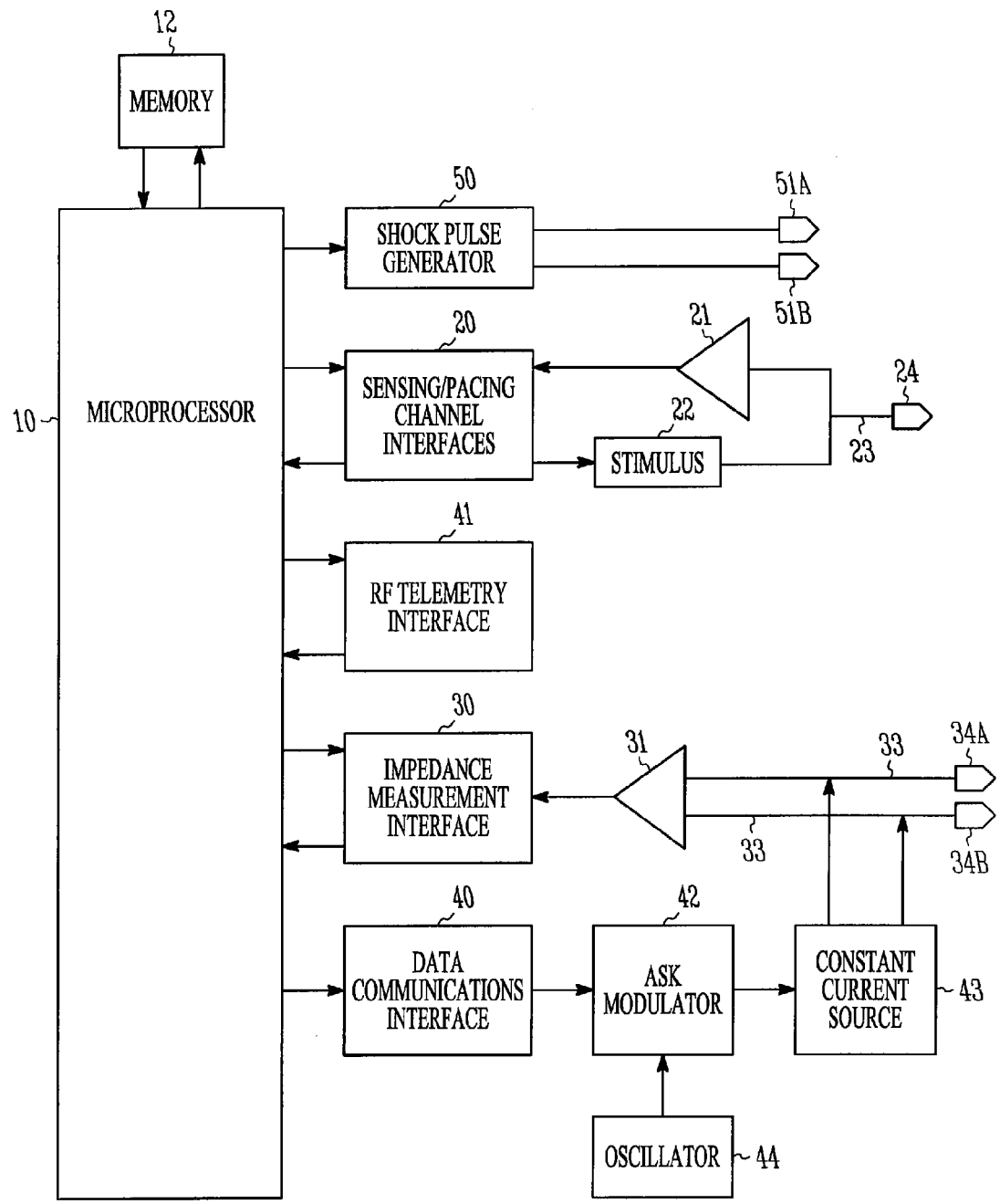
FIG. 1 is a system diagram of an exemplary implantable cardiac device.

The present invention is embodied by a data logging system in which an implantable medical device capable of sensing physiological and/or operational variables stores the sensed information in the form of a data log. Such a data log may include, for example, device/patient identifiers, data from sensing channels, and operating parameters. In the particular embodiment described below in detail, the implantable medical device is a cardiac device such as an implantable cardioverter/defibrillator, pacemaker, or combination device. Among the data that may be logged by such a device are electrogram data, pacing parameters, device status, cardiac output, and ventilation rate. The logged data is transmitted from the implantable device to the data logging device via a carrier waveform sensed by the data logging device at the skin surface. The logged data is encoded digitally and then used to modulate the carrier. The carrier waveform is generated by a means of an oscillating current produced between two electrodes disposed internally and in contact with body fluids. Such a current results in an oscillating dipole electric field that can be sensed externally as the potential difference between two electrodes in contact with the skin. As described below, a preferred embodiment employs as a carrier the same oscillating impedance measuring current used to measure minute ventilation and/or cardiac stroke volume.

The carrier waveform may be modulated with digitally encoded information by a variety of standard modulation techniques such as amplitude shift-keying, frequency shift-keying, phase shift-keying, and M-ary variants of those techniques. Because the impedance between the current injecting electrodes can vary (as, for example, in accordance with cardiac or lung volumes when the electrodes are disposed in a ventricle or elsewhere in the thorax), however, it is preferable to use a modulation technique that is unaffected by changes in the amplitude of the carrier. This is because such impedance variations between the electrodes can affect the potential at the skin surface resulting from a given amplitude of current.

One way to modulate the carrier with the digitally encoded information is to modulate a digital pulse train by varying the frequency, width, or position of the pulses, and then use the modulated pulse train to amplitude modulate the carrier waveform. The pulse train thus constitutes a sub-carrier. In a preferred embodiment, the pulse train is frequency modulated in accordance with the digitally encoded information so that the intervals between successive pulses are interpreted as symbols that signify a particular bit in the case of binary symbols, or a particular bit pattern in the case where more than two symbol states are used (i.e., M-ary modulation methods). In the embodiment described in detail below, the interval between each of the pulses of the pulse train is varied between two values to signify either a 1 or a 0. Each measured pulse interval thus constitutes a binary symbol. Alternate embodiments may employ additional intervals as symbol states in order to increase the data transmission rate. Since a pulse must only be sensed above a certain threshold in order to detect a symbol, this modulation scheme is unaffected by amplitude changes in the modulated carrier.

FIG. 1 is a system diagram of a microprocessor-based implantable cardioverter/defibrillator with the capability of also delivering pacing therapy. A microprocessor 10 communicates with a memory 12 and peripheral devices via bidirectional address and data busses. The memory 12 typically comprises a ROM or RAM for program storage and a RAM for data storage. The device has atrial and/or ventricular sensing and pacing channels for sensing depolarizations and delivering pacing pulses to the atria and/or ventricle. Each atrial/ventricular sensing and pacing channel comprises an electrode, lead, sensing amplifier, pulse generator, and a channel interface for communicating with the microprocessor 10, represented in the figure by electrode 24, lead 23, sensing amplifier 21, pulse generator 22, and a channel interface 20. A channel interface includes analog-to-digital converters for digitizing sensing signal inputs from the sensing amplifiers and registers which can be written to by the microprocessor in order to output pacing pulses, change the pacing pulse amplitude, and adjust the gain and threshold values for the sensing amplifiers. For each channel, the same lead and electrode are used for both sensing and pacing. The sensing channels are used in conjunction with pacing and for detecting arrhythmias. Also interfaced to the microprocessor is a shock pulse generator 50 for delivering cardioversion or defibrillation pulses to the heart via a pair of electrodes 51a and 51b, and a radio frequency telemetry interface 41 for communicating with an external programmer. A battery (not shown) supplies power to the device.

The device also has the capability of measuring the electrical impedance between electrodes 34a and 34b. A current is injected between the electrodes from constant current source 43, and the voltage between the electrodes is sensed and transmitted to the impedance measurement interface 30 through sense amplifier 31. The impedance measurement interface processes the voltage signal to extract the impedance information therefrom and communicates with the microprocessor. Depending upon where the electrodes 34a and 34b are disposed, the impedance measurement can be used to measure minute ventilation or cardiac stroke volume. An example of the latter is described in U.S. Pat. No. 5,190,035, issued to Salo et al., and hereby incorporated by reference.

In order to communicate logged data to the external data logging device, a current signal is generated between the electrodes 34a and 34b by driving the constant current source 43 with an oscillator 44. The waveform of the oscillator is modulated by an amplitude shift-keying (ASK) modulator 44 in accordance with the output of data communications interface 40. The data communications interface 40 receives digital data from the microprocessor 10 and frequency modulates a digital pulse train such that the interval between successive pulses is a binary symbol. The frequency modulated pulse train is then used as a subcarrier to modulate the carrier waveform. In this embodiment, the same current is used for both impedance measurement and data transmission to the external data logging device. Other embodiments may transmit information with current signals that are not also used for impedance measurement, in which case a constant current is not necessary.

Figure 2:
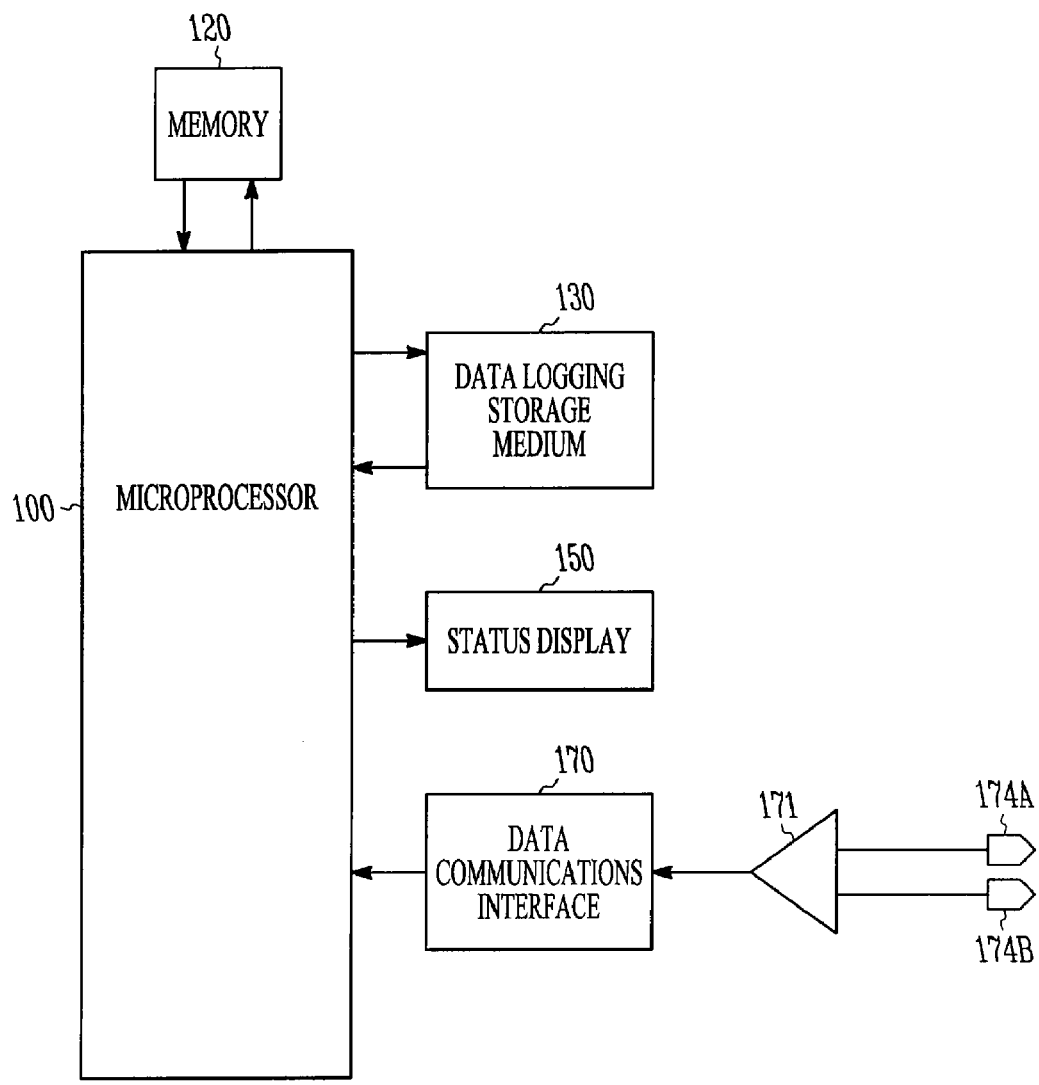
FIG. 2 is system diagram of the external data logging device.

FIG. 2 is a system diagram of an external data logging device for receiving data from the implantable cardiac device. The control circuitry of the device includes a microprocessor 100 and memory 120. A battery (not shown) supplies power to the device. Interfaced to the microprocessor is a data logging storage medium 130. The storage medium 130 is preferably a non-volatile memory such as a flash ROM. As the logging device receives logged data from the cardiac device, the data is stored in the medium 130 which can then be read to obtain the data log therefrom at some later time. In order to free up the storage medium for storage of subsequent data, the medium is either reused after extraction of the data or can be removed and replaced with another unit (e.g., removable flash ROM cards). A status display 150 is also interfaced to the microprocessor for displaying information to a user relating to the device's operating status such as battery power remaining and a log of received transmissions.

In order to receive information from the cardiac device, potentials are sensed at the skin surface between electrodes 174a and 174b by sensing amplifier 171. The output of amplifier 171 is input to data communications interface 170 which demodulates the sensed potentials to derive the digital signal encoded with logged data by the cardiac device. The digital signal is then processed by the microprocessor 100 and stored in the data logging storage medium. In this embodiment, the signal transmitted by the cardiac device is a carrier signal ASK modulated with a digital pulse train. The digital pulse train is used as a subcarrier by modulating the frequency of the pulses in accordance with a digital signal encoded with the logged data. The time interval between each successive pulse is one of two possible values to indicate a 1 or a 0 and thus constitutes a binary symbol.

Figure 3:
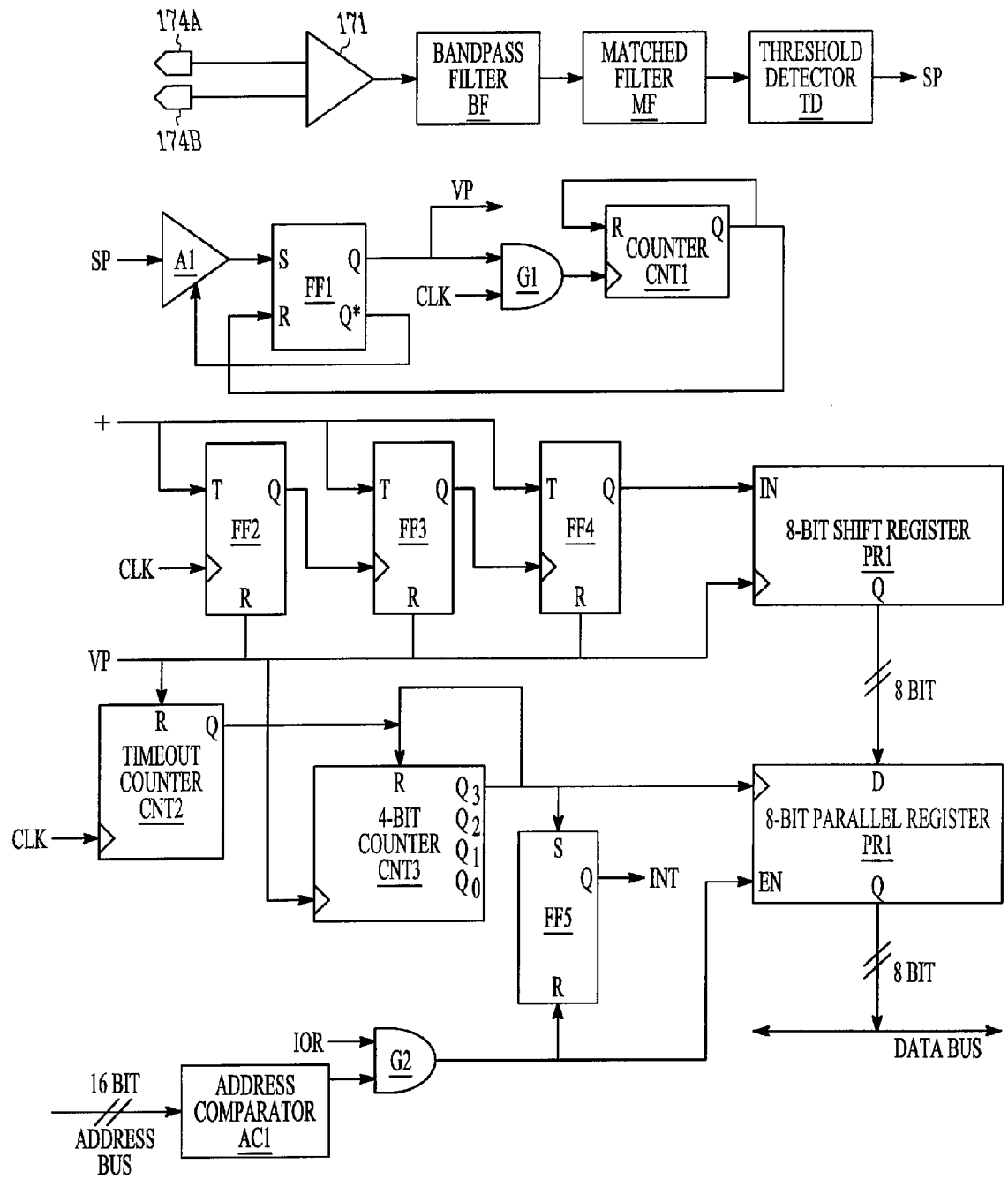
FIG. 3 is a circuit diagram of a data communications interface incorporated into the data logging device.

FIG. 3 is a high-level circuit diagram of the data communications interface 170. This particular embodiment uses discrete components to process the sensed potential signals, but the functionality could also be implemented by software executed by the microprocessor 100. The sensed potential signal from amplifier 171 is input to a bandpass filter BF that has its center frequency at the carrier signal frequency. In order to provide further noise immunity, the filtered signal is then input to a matched filter MF. The output of the matched filter MF is essentially a correlation between the sensed signal and a template signal corresponding to a transmitted pulse. The matched filter output is then compared with a specified threshold by threshold detector TD. If the threshold is exceeded, a sensed pulse signal SP compatible with the rest of the digital circuitry is output. The result of these steps is thus the ASK demodulation of the sensed carrier waveform. These operations may be performed by analog components or in the digital domain by processing digitized samples of the sensed signal.

As already noted, the time interval between each transmitted pulse and the preceding transmitted pulse is a symbol indicating either a 0 or a 1. In this embodiment, the interval between each pulse subcarrier pulse train is either T or 2T seconds such that the pulse frequency varies between 1/T and 1/2T Hz. Due to noise, however, the threshold detector TD may output sensed pulse signals separated by a much shorter interval. In order to avoid such spurious signals, only one sensed pulse SP within a specified limit time period is allowed to be regarded as a valid pulse and used to determine the interval symbol. A sensed pulse signal SP is input to a buffer A1 which either passes the signal or not in accordance with its tri-state enable input EN. If buffer A1 is enabled, the SP signal is passed to the set input S of flip-flop FF1. The Q output of FF1 is then asserted as a valid pulse signal VP which is decoded as a 1 or 0 by other circuitry using only the rising edge of VP. VP is maintained high for the limit time period until flip-flop FF1 is reset by the output of counter CNT1. When VP is asserted, AND gate G1 passes clock pulses CLK to the clock input of counter CNT1. When counter CNT1 has counted a number of clock pulses equal to the specified limit time period, the Q output of the counter corresponding to the limit time period is asserted which then resets flip-flop FF1 and the counter itself. Resetting of flip-flop FF1 deasserts the valid pulse signal VP which disables further clocking of counter CNT1 through gate G1 and readies the flip-flop for receipt of another sensed pulse signal SP. In order to ensure that VP is deasserted after timeout of the counter CNT1 so that another rising edge of VP can be output, the complementary output Q* of FF1 is used to tri-state disable the buffer A1 and prevent the setting of flip-flop FF1 until the flip-flop is reset by the Q output of counter CNT1. The rising edges of the signal VP thus correspond to the pulse train subcarrier which has been modulated with the digitally encoded data.

In order to demodulate the subcarrier, the rising edge of each asserted VP signal is used to detect a transmitted symbol in accordance with whether the time interval elapsed since the previous assertion of VP is T or 2T. In this embodiment, the period of the CLK signal is assumed to be 3T/8 so that the clock frequency is 8/3 times as fast as the fastest symbol rate 1/T of the transmitted signal. Flip-flops FF2, FF3, and FF4 are T-type flip-flops which together make up a divide-by-8 ripple counter clocked by the CLK signal so that the Q output of FF4 is a square wave of period 3T. The ripple counter is reset by each assertion of VP so that the Q output of FF4 transitions from low to high at a time 3T/2 after VP is asserted. This allows the next assertion of VP to use the output of the ripple counter as a data signal corresponding to the interval since the previous assertion of VP. That data signal is then clocked into a shift register SR1. A 0 is clocked into SR1 if the VP signal occurs earlier than time 3T/2 since the previous VP assertion, and a 1 is clocked in if the VP occurs between a time 3T/2 and 3T after the previous VP assertion when the ripple counter output is high. The time 3T/2 thus represents the mid-point between the two interval symbol states T and 2T. In this way, each VP pulse results in a 1 or a 0 being clocked into the shift register SR1 in accordance with the time interval since the previous VP pulse. Note that if no previous VP pulse has been received, the first VP pulse clocks an indeterminate value into the shift register and should be disregarded.

Shift register SR1 is an 8-bit register so that the register is full after eight VP assertions, and the data contained therein must to transferred elsewhere. Counter CNT3 is a 4-bit counter clocked by the rising edge of VP so that its most significant bit output $Q_3$ is asserted after eight assertions of VP. $Q_3$ is tied to the clock input of 8-bit parallel register PR1 so that its assertion loads the 8-bit output of shift register SR1 into register PR1. Assertion of $Q_3$ also resets the counter CNT3. In this manner, the demodulated data contained in shift register SR1 is transferred to register PR1 after every eight assertions of VP. A timeout counter CNT2 is also clocked by CLK with its Q output corresponding to a specified timeout period used to reset counter CNT3. Thus, in the event that no VP assertion is received after the specified timeout period, the framing of data into 8-bit bytes is restarted with the next VP pulse.

Assertion of $Q_3$ also sets flip-flop FF5 which causes assertion of an interrupt signal INT to the microprocessor signifying that the data contained in register PR1 is available for reading. The interrupt servicing routine then accesses the register PR1 by putting its address on the address bus which causes the output of address comparator AC1 to go high. AND gate G2 then passes the assertion of a read strobe IOR to enable the tri-state outputs of register PR1 and puts its 8-bit contents onto the data bus. The read strobe IOR also resets the flip-flop FF5 to clear the interrupt signal. After reading the data contained in the register PR1 and verifying it to be valid, the microprocessor stores the data in the storage medium 130.

Data is thus received by the microprocessor in the form of consecutive 8-bit bytes. Such data can include error-correcting codes in order for the microprocessor to determine whether the data should be regarded as valid information. The cardiac device may repeat each transmission a specified number of times in order to increase the probability that a valid transmission is received. The data can be segregated into separate frames for this purpose with the beginning and end of each frame signified by particular data bytes.

Figure 4:
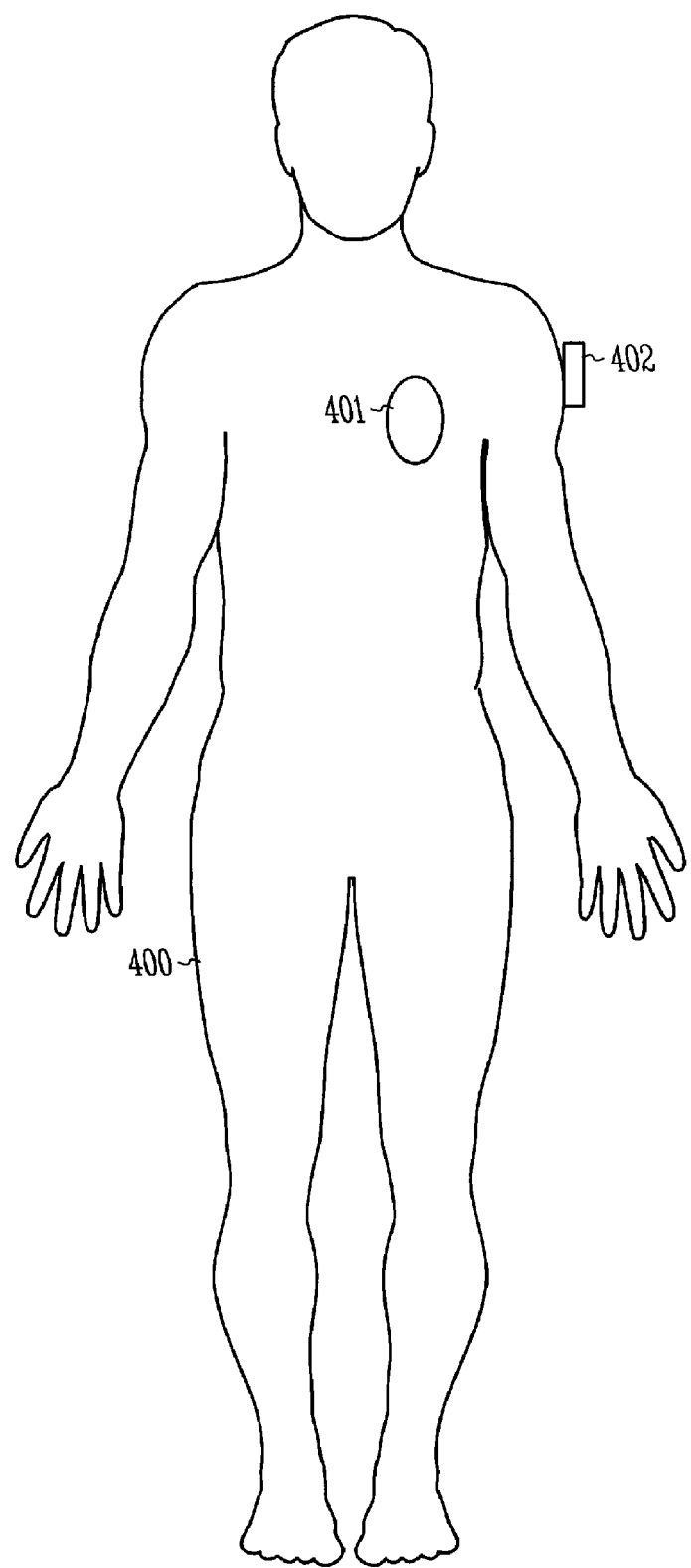
FIG. 4 depicts an exemplary physical placement of an implantable cardiac device and an external data logging device.
Figure 5:
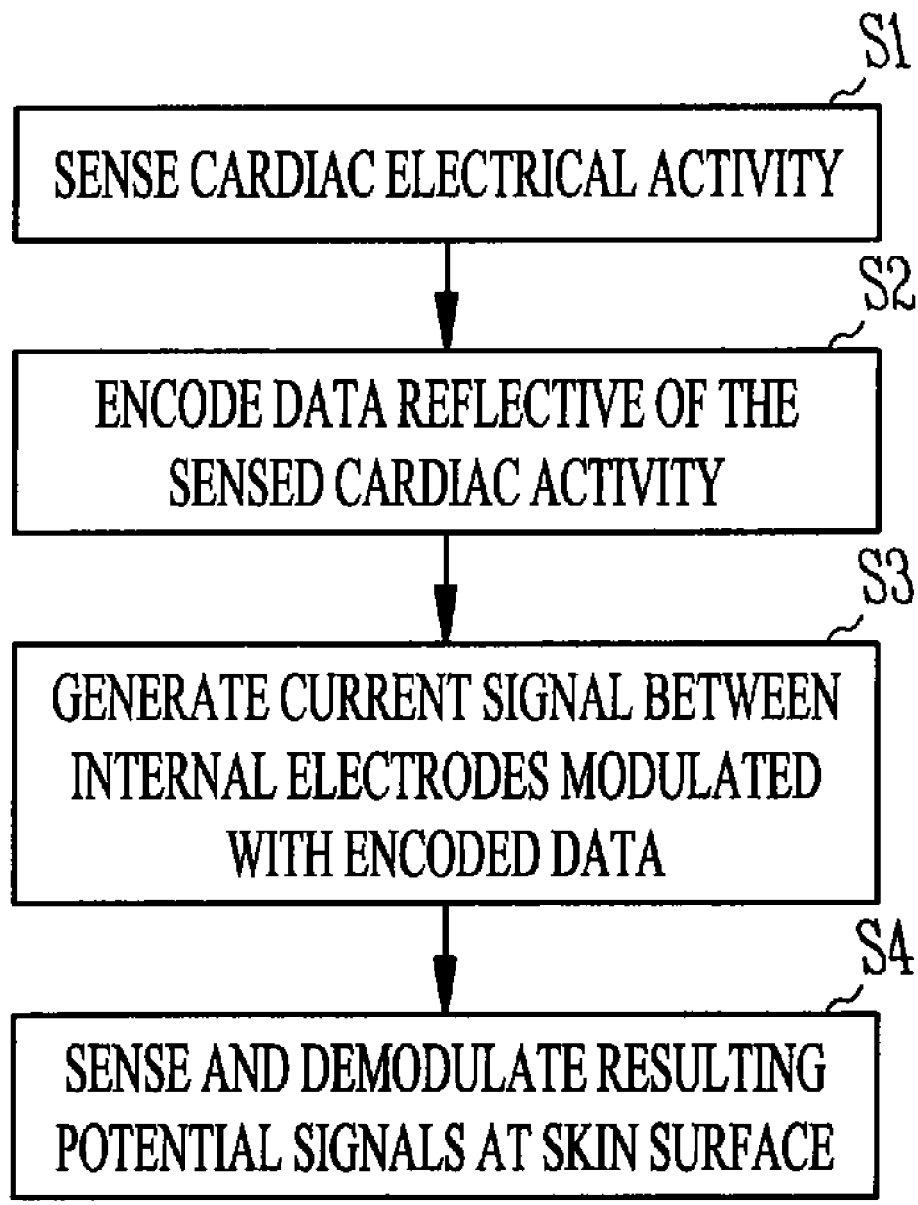
FIG. 5 illustrates the steps performed in transmitting data from an implantable device to an external data logging device.

FIG. 4 depicts an exemplary physical placement of an implantable cardiac device 401 in a patient 400 and an external data logging device 402 affixed to a skin surface location. FIG. 5 illustrates an example of the steps performed in transmitting data from an implantable cardiac device to an external data logging device. At step S1, the implantable cardiac device senses cardiac activity and encodes data reflective of the sensed cardiac activity at step S2. At step S3, the implantable device generates a current signal between internal electrodes modulated with the encoded data. At step S4, the external data logging device senses and demodulates the resulting potential signals at a skin surface location.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. A data logging system, comprising:
   an implantable medical device having a constant current source connected to two electrodes adapted for internal disposition and contact with body fluids, the current source being driven by an oscillator for producing a current signal modulated with encoded data between the two electrodes to cause corresponding modulated potential signals detectable at a skin surface; and,
   an external data logging device for affixation to a patient having incorporated therein a data communications interface for demodulating potential signals sensed at a skin surface location to extract encoded data therefrom, and circuitry for storing the encoded data in a data logging storage medium.

2. The system of claim 1 wherein the implantable medical device is a cardiac device with a sensing channel for sensing cardiac electrical activity and further wherein data reflective of the sensed cardiac activity can be encoded and transmitted to the external data logging device.

3. The system of claim 2 wherein the potential signals are transmitted in the form of a carrier waveform digitally modulated with the digitally encoded data by varying the amplitude of the carrier waveform.

4. The system of claim 2 wherein the potential signals are transmitted in the form of a carrier waveform digitally modulated with the digitally encoded data by varying the frequency of the carrier waveform.

5. The system of claim 2 wherein the potential signals are transmitted in the form of a digital pulse train modulated with the digitally encoded data by varying the frequency of the pulses and amplitude modulating a carrier waveform with the modulated pulse train.

6. The system of claim 2 wherein the potential signals are transmitted in the form of a digital pulse train modulated with the digitally encoded data by varying the width of the pulses and amplitude modulating a carrier waveform with the modulated pulse train.

7. The system of claim 2 wherein the potential signals are transmitted in the form of a digital pulse train modulated with the digitally encoded data by varying the position of the pulses and amplitude modulating a carrier waveform with the modulated pulse train.

8. The system of claim 2 wherein the implantable cardiac device comprises circuitry for performing an impedance measurement related to a physiological variable by injecting current between two electrodes from a constant current source and further wherein the constant current source is used for transmitting potential signals modulated with digitally encoded data to the external data logging device.

9. The system of claim 2 wherein the data logging storage medium of the external data logging device is removable.

10. The system of claim 9 wherein the data logging storage medium is a flash ROM.

11. A method for data logging comprising:
    sensing cardiac electrical activity with an implanted cardiac device;
    encoding data reflective of the sensed cardiac activity;
    driving a constant current source connected to two internally disposed electrodes in contact with body fluids, the current source being driven by an oscillator for producing a current signal modulated with encoded data between the two electrodes to cause corresponding electrical potentials that can be sensed at a skin surface location;
    receiving and demodulating sensed potential signals at a skin surface location to derive the encoded data therefrom; and,
    storing the derived encoded data in a data logging storage medium of an external data logging device.

12. The method of claim 11 further comprising removing and replacing the data logging storage medium at periodic intervals.

13. The method of claim 11 further comprising transmitting the potential signals in the form of a carrier waveform digitally modulated with the digitally encoded data by varying the amplitude of the carrier waveform.

14. The method of claim 11 further comprising transmitting the potential signals in the form of a carrier waveform digitally modulated with the digitally encoded data by varying the frequency of the carrier waveform.

15. The method of claim 11 further comprising transmitting the potential signals in the form of a digital pulse train modulated with the digitally encoded data by varying the frequency of the pulses and amplitude modulating a carrier waveform with the modulated pulse train.

16. The method of claim 11 further comprising transmitting the potential signals in the form of a digital pulse train modulated with the digitally encoded data by varying the width of the pulses and amplitude modulating a carrier waveform with the modulated pulse train.

17. The method of claim 11 further comprising transmitting the potential signals in the form of a digital pulse train modulated with the digitally encoded data by varying the position of the pulses and amplitude modulating a carrier waveform with the modulated pulse train.

18. The method of claim 11 further comprising performing an impedance measurement related to a physiological variable by injecting current between two electrodes from a constant current source and using the constant current source for transmitting potential signals modulated with encoded data to the external data logging device.

* * * * *